(12) United States Patent
Ozer et al.

(10) Patent No.: US 8,398,728 B2
(45) Date of Patent: Mar. 19, 2013

(54) PROCESS FOR MAKING A COMPOSITION COMPRISING AT LEAST TWO DIFFERENT DIALKYL ETHERS

(75) Inventors: Ronnie Ozer, Arden, DE (US); Michael B. D'Amore, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 290 days.

(21) Appl. No.: 12/742,282

(22) PCT Filed: Nov. 13, 2008

(86) PCT No.: PCT/US2008/083308
§ 371 (c)(1),
(2), (4) Date: May 11, 2010

(87) PCT Pub. No.: WO2009/064828
PCT Pub. Date: May 22, 2009

(65) Prior Publication Data
US 2010/0251609 A1 Oct. 7, 2010

Related U.S. Application Data

(60) Provisional application No. 61/002,816, filed on Nov. 13, 2007.

(51) Int. Cl.
*C10L 1/18* (2006.01)
(52) U.S. Cl. .......... 44/448; 568/579; 568/671; 568/698; 568/699
(58) Field of Classification Search .................... 44/448; 568/579, 671, 698, 699
See application file for complete search history.

(56) References Cited

U.S. PATENT DOCUMENTS 6,323,383 B1 * 11/2001 Tsuchida et al. ............... 585/601
6,824,574 B2 * 11/2004 O'Rear et al. .................. 44/448

FOREIGN PATENT DOCUMENTS

| EP | 1185492 A | 3/2002 |
|---|---|---|
| EP | 1829851 A | 9/2007 |
| GB | 381185 A | 9/1932 |
| GB | 939686 A | 10/1963 |
| JP | 115158102 | * 6/1999 |

OTHER PUBLICATIONS

International Search Report and Written Opinion, International Application No. PCT/US2008/083308, International Filing Date: Nov. 13, 2008.
WO92/13819 Henkel KGAA (DE) Aug. 20, 1992.

* cited by examiner

*Primary Examiner* — Cephia D Toomer
(74) *Attorney, Agent, or Firm* — Kevin S. Dobson

(57) ABSTRACT

The present invention further contemplates a process for making a dialkyl ether composition comprising two or more ethers of the formula $R^1$—O—$R^2$. The present invention further contemplates a process for making a dialkyl ether composition starting from a first reaction product comprising 1-butanol. The invention further contemplates a dialkyl ether composition comprising two or more ethers of the formula $R^1$—O—$R^2$, where each $R^1$ and $R^2$ can independently be any carbon chain length, saturated or unsaturated; branched or straight-chain, of between $C_2$ and $C_{10}$; specifically between $C_4$ and $C_{10}$; more specifically between $C_4$ and $C_6$; more specifically $C_6$; more specifically $0_4$. The present invention further contemplates a process where a first reaction product comprising 1-butanol is used to produce a dialkyl ether composition where each $R^1$ and $R^2$ can independently be any carbon chain length, saturated or unsaturated; branched or straight-chain, of between $C_2$ and $C_{10}$; specifically between $C_4$ and $C_{10}$; more specifically between $C_4$ and $C_6$; more specifically $C_6$; more specifically $C_4$.

10 Claims, No Drawings

PROCESS FOR MAKING A COMPOSITION COMPRISING AT LEAST TWO DIFFERENT DIALKYL ETHERS

CROSS-REFERENCE TO RELATED APPLICATIONS

This application claims benefit of priority from Provisional Application No. 61/002,816, filed Nov. 13, 2007.

FIELD OF THE INVENTION

The present invention relates to a process for making a composition comprising at least two different ethers using ethanol, or a combination of ethanol and methanol as a starting material.

BACKGROUND

Dialkyl ethers are known to be useful as diesel fuel cetane enhancers. For example published patent application WO2001/018154 discloses a diesel fuel formulation comprising dibutyl ether. Dibutyl ethers may be produced from butanol and the reaction is generally carried out via the dehydration of n-butyl alcohol by sulfuric acid, or by catalytic dehydration over ferric chloride, copper sulfate, silica, or silica-alumina at high temperatures (see for example, Karas, L. and Piel, W. J., *Ethers*, in Kirk-Othmer Encyclopedia of Chemical Technology, Fifth Ed., Vol. 10, Section 5.3, p. 576).

It is widely known that ethanol can be recovered from a number of sources, including synthetic and fermentation feedstocks. Methods for producing 1-butanol from ethanol are known as well. It is also known that 1-butanol can be prepared by condensation from ethanol over basic catalysts at high temperature using the so-called "Guerbet Reaction" (see for example, J. Logsdon in Kirk-Othmer Encyclopedia of Chemical Technology, John Wiley and Sons, Inc., New York, 2001). The production of transportation fuels from ethanol is widely accepted in the gasoline market; however the production of diesel fuel or fuel additives from ethanol has not been described. In addition, dialkyl ethers derived from ethanol can provide an advantage over petroleum based diesel and vegetable or animal fat based diesel in the reduction of greenhouse gas emissions and reducing reliance on scarce petroleum reserves.

The production of dibutyl ethers from butanol has been described in the prior art, however, the process for making these dibutyl ethers from butanol and other alcohols synthesized from ethanol over a base catalyst has not been described. The present invention provides a route to a dialkyl ether composition comprising a mixture of dialkyl ethers useful as a fuel additive providing an alternative to traditional petroleum sources.

SUMMARY OF THE INVENTION

An embodiment provides a process for making a dialkyl ether composition comprising two or more ethers of the formula $R^1$—O—$R^2$, wherein each $R^1$ and $R^2$ is independently $C_2$-$C_{10}$ straight-chain or branched alkyl groups, comprising:

a) contacting a reactant comprising ethanol with a base catalyst to make a first reaction product comprising 1-butanol and water, and optionally comprising unreacted ethanol;

b) optionally removing a substantial portion of the water from said first reaction product;

c) optionally removing a substantial portion of the unreacted ethanol from said first reaction product;

d) contacting the product of either step (a), step (b), step (c), or steps (b) and (c), optionally in the presence of a solvent, with at least one acid catalyst at a temperature of about 50° C. to about 450° C. and a pressure from about 0.1 MPa to about 20.7 MPa to produce a second reaction product comprising two or more ethers of the formula $R^1$—O—$R^2$; and e) recovering said dialkyl ether composition from said second reaction product.

In yet another embodiment, the process, wherein each $R^1$ and $R^2$ is independently $C_4$-$C_{10}$ straight-chain or branched alkyl.

In yet another embodiment, the process, wherein each $R^1$ and $R^2$ is independently $C_4$-$C_6$ straight-chain or branched alkyl.

In yet another embodiment, the process, wherein each $R^1$ and $R^2$ is independently $C_6$ straight-chain or branched alkyl.

Another embodiment provides the process, wherein each $R^1$ and $R^2$ is independently $C_4$ straight-chain or branched alkyl.

Another embodiment provides the process, wherein the acidic catalyst is a homogenous catalyst.

Another embodiment provides the process, wherein the homogenous catalyst is a sulfonic acid.

In yet another embodiment, the process, wherein the acidic catalyst is a heterogeneous catalyst.

Another embodiment provides the process, wherein the heterogeneous catalyst is selected from the group consisting of heterogeneous heteropolyacids, natural clay minerals, cation exchange resins, metal oxides, mixed metal oxides, metal salts, zeolites, and mixtures thereof.

In yet another embodiment, the process, wherein the heterogeneous catalyst is selected from the group consisting of perfluorinated ion-exchange polymer (PFIEP), ion-exchange resin, and zeolite.

In yet another embodiment, the process, wherein the temperature is from about 100° C. to about 250° C.

Another embodiment provides the process, wherein the pressure is from about 0.1 MPa to about 3.45 MPa.

In yet another embodiment, the process, wherein the dialkyl ether is recovered by phase separation.

In yet another embodiment, the process, wherein the dialkyl ether is recovered by distillation.

Another embodiment provides the process, wherein the dialkyl ether is recovered by extraction with a suitable solvent.

An embodiment provides a process for making a dialkyl ether composition comprising two or more ethers of the formula $R^3$—O—$R^4$, wherein each $R^3$ and $R^4$ is independently $C_1$-$C_{10}$ straight-chain or branched alkyl groups, comprising:

a) contacting a reactant comprising ethanol and methanol with a base catalyst to make a first reaction product comprising at least one $C_3$-$C_{10}$ straight-chain or branched alkyl alcohol and water, and optionally comprising unreacted reactant;

b) optionally removing a substantial portion of the water from said first reaction product;

c) optionally removing a substantial portion of the unreacted reactant from said first reaction product;

d) contacting the product of either step (a), step (b), step (c), or steps (b) and (c), optionally in the presence of a solvent, with at least one acid catalyst at a temperature of about 50° C. to about 450° C. and a pressure from about 0.1 MPa to about 20.7 MPa to produce a second reaction product comprising two or more ethers of the formula $R^3$—O—$R^4$; and e) recovering said dialkyl ether composition from said second reaction product.

Another embodiment provides the process, wherein the alcohol is between $C_4$-$C_6$ straight-chain or branched alkyl.

Another embodiment provides the process, wherein each $R^3$ and $R^4$ is independently $C_4$-$C_{10}$ branched or straight-chain alkyl.

In yet another embodiment, the process, wherein each $R^1$ and $R^2$ is independently $C_4$-$C_6$ straight-chain or branched alkyl.

In yet another embodiment, the process, wherein each $R^1$ and $R^2$ is independently $C_6$ chain or branched alkyl.

Another embodiment provides the process, wherein each $R^1$ and $R^2$ is independently $C_4$ straight-chain or branched alkyl.

In yet another embodiment, the process, wherein the temperature is from about 100° C. to about 250° C.

In yet another embodiment, the process, wherein the pressure is from about 0.1 MPa to about 3.45 MPa.

Another embodiment provides the process, wherein the dialkyl ether is recovered by phase separation.

Another embodiment provides the process, wherein the dialkyl ether is recovered by distillation.

In yet another embodiment, the process, wherein the acidic catalyst is a homogenous catalyst.

Another embodiment provides the process, wherein the homogenous catalyst is a sulfonic acid.

In yet another embodiment, the process, wherein the acidic catalyst is a heterogeneous catalyst.

In yet another embodiment, the process wherein the heterogeneous catalyst is selected from the group consisting of heterogeneous heteropolyacids, natural clay minerals, cation exchange resins, metal oxides, mixed metal oxides, metal salts, zeolites, and mixtures thereof.

In yet another embodiment, the process, wherein the heterogeneous catalyst is selected from the group consisting of perfluorinated ion-exchange polymer (PFIEP), ion-exchange resin, and zeolite.

Another embodiment provides the process, wherein ethanol is obtained by fermentation.

An embodiment of the invention provides a composition for use as diesel fuel or fuel additive comprising the reaction product of the process comprising:

a) contacting a reactant comprising ethanol or ethanol and methanol with a base catalyst to make a first reaction product comprising at least one $C_3$-$C_{10}$ straight-chain or branched alkyl alcohol and water, and optionally comprising unreacted reactant;

b) optionally removing a substantial portion of the water from said first reaction product;

c) optionally removing a substantial portion of the unreacted reactant from said first reaction product;

d) contacting the product of either step (a), step (b), step (c), or steps (b) and (c), optionally in the presence of a solvent, with at least one acid catalyst at a temperature of about 50° C. to about 450° C. and a pressure from about 0.1 MPa to about 20.7 MPa to produce a second reaction product comprising two or more ethers of the formula $R^5$—O—$R^6$, wherein each $R^5$ and $R^6$ is independently $C_1$-$C_{10}$ or $C_2$-$C_{10}$ straight-chain or branched alkyl groups; and e) recovering said dialkyl ether composition from said second reaction product.

Another embodiment provides the process, wherein the alcohol is between $C_4$-$C_6$ straight-chain or branched alkyl.

In yet another embodiment, the process, wherein each $R^5$ and $R^6$ is independently $C_4$-$C_6$ straight-chain or branched alkyl.

In yet another embodiment, the process, wherein each $R^5$ and $R^6$ is independently $C_6$ chain or branched alkyl.

Another embodiment provides the process, wherein each $R^5$ and $R^6$ is independently $C_4$ straight-chain or branched alkyl.

In yet another embodiment, the process, wherein the temperature is from about 100° C. to about 250° C.

In yet another embodiment, the process, wherein the pressure is from about 0.1 MPa to about 3.45 MPa.

In yet another embodiment, the process, wherein the acidic catalyst is a homogenous catalyst.

Another embodiment provides the process, wherein the homogenous catalyst is a sulfonic acid.

In yet another embodiment, the process, wherein the acidic catalyst is a heterogeneous catalyst.

An embodiment provides the process, wherein ethanol is obtained by fermentation.

DETAILED DESCRIPTION

The present invention relates to a process for making a dialkyl ether composition. Useful applications for the dialkyl ether composition include the addition of the composition to a transportation fuel as a fuel additive. The dialkyl ethers represent an advantage over petroleum diesel fuels as they can be produced from ethanol. Ethanol is useful on the large as a manufactured fuel, as well as a fuel additive, produced from renewable resources such as corn, sugar cane or cellulosic feeds. In addition dialkyl ethers offer cetane and cloud point improvements compared to traditional biodiesel or petroleum diesel. In countries where ethanol production is operated at large scale such as Brazil, the ability to produce diesel fuel from ethanol offers an advantage. The present invention provides a dialkyl ether composition comprising a mixture of dialkyl ethers which are useful as a fuel additive. The composition is useful as an additive or blend component to diesel fuel. The composition is also useful as a cetane enhancer for diesel fuel, providing a lower cloud point for diesel fuel. With government regulation requiring higher levels of non-fossil fuels in the diesel market, dialkyl ethers offer an alternative to vegetable and animal fat based alternative diesel fuels currently in use and limited in their utility. For example, dialkyl ethers can be added to diesel fuels at levels of 10% without negatively impacting performance, whereas conventional additive FAME (fatty acid methyl esters) materials are generally limited to 5% in diesel because of performance and cold flow properties. Dialkyl ethers derived from ethanol produced from biomass also have the ability to replace a portion of the petroleum based diesel supply. In light of the world's need to find alternative fuel sources utilizing potentially synthetic and fermentative feedstock, there is a need for fuel additives which are low cost and are an alternative to traditional fossil fuels. Current world supply of such alternative fuels for the diesel market is limited to the use of FAME biodiesel produced from vegetable and animal fats.

The following definitions are used herein and should be referred to for interpretation of the claims and the specification.

The term "dialkyl ether composition" means a mixture of two or more dialkyl ethers.

The term "base catalyst" means either a substance which has the ability to accept protons as defined by Brönsted, or a substance which has an unshared electron pair with which it can form a covalent bond with an atom, molecule or ion as defined by Lewis.

The term "unreacted ethanol" refers to ethanol which has not been chemically reacted to another compound.

The term "hydrotalcites" refers to layered, double hydroxides of the general formula

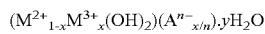

The $M^{2+}$ ions can be a variety of divalent cations (e.g., Mg, Ni, Pt, Pd, Zn, Co, Fe, Cu) and the $M^{3+}$ ions can be trivalent Al, Fe or Cr. Some hydrotalcites are described by V. K. Diez, C. R. Apesteguia, and J. I. DiCosimo (*Latin American Applied Research*, 33, 79-86 (2003)) and N. N. Das and S. C. Srivastava (*Bull. Mater. Sci.* 25, (4), 283-289 (2002)).

The term, "° C." means degrees Celsius.
The term "mg" means milligram.
The term "min" means minutes.
The term "mL" means milliliter.
The term "temp" means temperature.
The term "MPa" means mega Pascal.
The term "GC/MS" means gas chromatography/mass spectrometry.

GENERAL METHODS AND MATERIALS

The reactant component comprising ethanol can be obtained from any convenient source. For example, ethanol may be obtained synthetically by direct catalytic hydration of ethylene, indirect hydration of ethylene, conversion of synthesis gas (carbon monoxide and hydrogen), homologation of methanol, carbonylation of methanol and methyl acetate as is known in the art. The reactant comprising ethanol may also be obtained by fermentation, however, the fermentative microorganism and the source of its substrate are not critical for the purposes of this invention. For example, ethanol may be produced fermentatively by the yeast *Saccharomyces cerevisiae* or the bacterium *Zymomonas mobilis* using sugars, optionally obtained from cellulosic materials as the carbon and energy source for growth. The result of the fermentation is a fermentation broth, which is then refined to produce a stream of aqueous ethanol. The refining process may comprise at least one distillation column by which an overhead stream comprising an azeotrope of ethanol and water is produced, and whereby the removal of solids, such as cell biomass, unconsumed complex sugars, and precipitated salts or proteins, from the fermentation broth is effected. Once the ethanol-water azeotrope has been distilled off, the ethanol-water azeotrope can be used as the reactant for the present invention, or one or more drying procedures can be performed to reduce the amount of water in the overhead stream. While many drying methods are known, generally the reaction product (in this case, ethanol) is passed over a desiccant, such as molecular sieves, until the desired amount of water has been removed.

In one embodiment, the reactant comprising ethanol (which may be diluted with an inert gas such as nitrogen, carbon dioxide, or mixtures thereof) is then contacted with at least one base (also referred to as "basic") catalyst in the vapor or liquid phase at a temperature of about 150° C. to about 500° C. and at a pressure from about 0.1 MPa to about 20.7 MPa to produce a first reaction product comprising 1-butanol and water. Typically, the first reaction product will also comprise unreacted ethanol and a variety of organic products. The organic products include butanols other than 1-butanol; as well as higher alcohols, such as hexanols or octanols.

Base catalysts useful in practicing the present invention may be homogeneous or heterogeneous catalysts. Homogeneous catalysis is catalysis in which all reactants and the catalyst are molecularly dispersed in one phase. Heterogeneous catalysis refers to catalysis in which the catalyst constitutes a separate phase from the reactants and products.

A suitable base catalyst useful in the current process is either a substance which has the ability to accept protons as defined by Brönsted, or a substance which has an unshared electron pair with which it can form a covalent bond with an atom, molecule or ion as defined by Lewis.

Examples of suitable base catalysts include, but are not limited to, metal oxides, hydroxides, amides, oxynitrides, fluorides, carbonates, silicates, phosphates, aluminates and combinations thereof. Preferred base catalysts are metal oxides, carbonates, silicates, and phosphates. Preferred metals of the aforementioned compounds are selected from Group 1, Group 2, and rare earth elements of the Periodic Table. Particularly preferred metals are cesium, rubidium, calcium, magnesium, aluminum, lithium, barium, potassium, zirconium and lanthanum.

The base catalyst may be supported on a catalyst support, as is common in the art of catalysis. Suitable catalyst supports include, but are not limited to, alumina, titania, silica, zirconia, zeolites, carbon, clays, double-layered hydroxides, hydrotalcites and combinations thereof. Any method known in the art to prepare the supported catalyst can be used. One method for preparing supported catalysts is to dissolve a metal carboxylate salt in water. A support such as silica is wetted with the dissolved metal carboxylate salt solution, and then calcined. This process converts the supported metal carboxylate to the metal oxide, carbonate, hydroxide or combination thereof. The catalyst support can be neutral, acidic or basic, as long as the surface of the catalyst/support combination is basic. Commonly used techniques for treatment of supports with metal catalysts can be found in B. C. Gates, *Heterogeneous Catalysis*, Vol. 2, pp. 1-29, Ed. B. L. Shapiro, Texas A & M University Press, College Station, Tex., 1984.

The base catalysts of the present invention may further comprise catalyst additives and promoters that will enhance the efficiency of the catalyst. The relative percentage of the catalyst promoter may vary as desired. Promoters may be selected from the Group 8 metals of the Periodic Table, as well as copper and chromium.

The base catalysts of the present invention can be obtained commercially, or can be prepared from suitable starting materials using methods known in the art. An embodiment of the invention provides catalysts to be used in the form of powders, granules, or other particulate forms. Selection of an optimal average particle size for the catalyst will depend upon such process parameters as reactor residence time and desired reactor flow rates.

The catalytic conversion of the reactant to the first reaction product and water can be run in either batch or continuous mode. Suitable reactors include fixed-bed, adiabatic, fluid-bed, transport bed, and moving bed. During the course of the reaction, the catalyst may become fouled, and therefore it may be necessary to regenerate the catalyst. Preferred methods of catalyst regeneration include contacting the catalyst with a gas such as, but not limited to, air, steam, hydrogen, nitrogen or combinations thereof, at an elevated temperature.

One skilled in the art will know that conditions, such as temperature, catalytic metal, support, reactor configuration and reaction time can affect the reaction kinetics, product yield and product selectivity. Consequently standard experimentation can be used to optimize the yield of alcohols in the first reaction product.

The first reaction product can optionally be subjected to a suitable refining process, such as distillation, to remove a substantial portion of the water present in the first reaction product, or to remove unreacted ethanol using well-known chemical engineering techniques. If the first reaction product is subjected to a refining process, the resulting product is referred to hereinafter as the "refined first reaction product". As used herein, the term "substantial" means fairly large, greater than 90 wt % of the water and ethanol, that is, more than minor or trivial.

The present invention further contemplates a process for making a dialkyl ether composition comprising two or more ethers of the formula $R^1$—O—$R^2$. The present invention further contemplates a process for making a dialkyl ether composition starting a first reaction product 1-butanol. The invention further contemplates a dialkyl ether composition comprising two or more ethers of the formula $R^1$—O—$R^2$, where each $R^1$ and $R^2$ can independently be any carbon chain length, saturated or unsaturated; branched or straight-chain, of between $C_2$ and $C_{10}$; specifically between $C_4$ and $C_{10}$; more specifically between $C_4$ and $C_6$; more specifically $C_6$; more specifically $C_4$. The present invention further contemplates a process where a first reaction product 1-butanol is used to produce a dialkyl ether composition where each $R^1$ and $R^2$ can independently be any carbon chain length, saturated or unsaturated; branched or straight-chain, of between $C_2$ and $C_{10}$; specifically between $C_4$ and $C_{10}$; more specifically between $C_4$ and $C_6$; more specifically $C_6$; more specifically $C_4$.

The acid-catalyzed reaction to form the dialkyl ether composition can be performed at a temperature of from about 50° C. to about 450° C. In a more specific embodiment, the temperature is from about 100° C. to about 250° C. The reaction can be carried out under an inert atmosphere at a pressure of from about atmospheric pressure (about 0.1 MPa) to about 20.7 MPa. In a more specific embodiment, the pressure is from about 0.1 MPa to about 3.45 MPa. Suitable inert gases include nitrogen, argon, helium, or mixtures thereof.

The acid catalyst can be a homogeneous (unsupported) or heterogeneous (supported) catalyst. Homogeneous acid catalysts include, but are not limited to inorganic acids, organic sulfonic acids, heteropolyacids, fluoroalkyl sulfonic acids, metal sulfonates, metal trifluoroacetates, compounds and combinations. Examples of homogeneous acid catalysts include, but are not limited to, sulfuric acid, fluorosulfonic acid, phosphoric acid, p-toluenesulfonic acid, benzenesulfonic acid, hydrogen fluoride, phosphotungstic acid, phosphomolybdic acid, and trifluoromethanesulfonic acid, nonafluorobutanesulfonic acid, 1,1,2,2-tetrafluoroethanesulfonic acid and 1,1,2,3,3,3-hexafluoropropanesulfonic acid.

Heterogeneous acid catalysts include, but are not limited to (1) heterogeneous heteropolyacids (HPAs), (2) natural clay minerals, such as those containing alumina or silica, (3) cation exchange resins, (4) metal oxides, (5) mixed metal oxides, (6) metal salts such as metal sulfides, metal sulfates, metal sulfonates, metal nitrates, metal phosphates, metal phosphonates, metal molybdates, metal tungstates, metal borates, (7) zeolites, and (8) combinations of groups (1) to (7). See, for example, Solid Acid and Base Catalysts, pages 231-273 (Tanabe, K., in Catalysis: Science and Technology, Anderson, J. and Boudart, M (eds.) 1981 Springer-Verlag, New York) for a description of solid catalysts.

Suitable heterogeneous acid catalysts include perfluorinated ion-exchange polymers (PFIEP), ion-exchange resins such as Amberlyst® (commercially available from Rohm and Haas, Philadelphia, Pa.), and zeolites, such as CBV-3020E (commercially available from PQ Corporation, Berwyn, Pa.). Representative of the perfluorinated ion-exchange polymers for use in the present invention are "NAFION®" PFIEP (commercially available from E. I. du Pont de Nemours and Company), and polymers, or derivatives of polymers, disclosed in U.S. Pat. No. 3,282,875. More preferably the polymer comprises a perfluorocarbon backbone and a pendant group represented by the formula —OCF$_2$CF(CF$_3$) OCF$_2$CF$_2$SO$_3$X, wherein X is H, an alkali metal or NH$_4$. Polymers of this type are disclosed in U.S. Pat. No. 3,282,875.

Suitable heterogeneous catalysts also include porous PFIEP microcomposites comprising a PFIEP-containing pendant sulfonic acid and/or carboxylic acid groups entrapped within and highly dispersed throughout a network of metal oxide, a network of silica or a network of metal oxide and silica as described in U.S. Pat. No. 5,824,622.

One skilled in the art will know that conditions such as temperature, catalytic metal, support, reactor configuration and reaction time can affect the reaction kinetics, product yield and product selectivity. Depending on the reaction conditions, such as the particular catalyst used, products other than ethers may be produced when the first reaction product comprising 1-butanol or the refined reaction product is contacted with an acid catalyst. Additional products produced comprise butenes and isooctenes. Standard experimentation can be used to optimize the yield of ethers from the reaction.

Following the reaction, if necessary, the catalyst can be separated from the second reaction product by any suitable technique known to those skilled in the art, such as decantation, filtration, extraction or membrane separation.

The dialkyl ether composition can be recovered from the second reaction product by distillation. Alternatively, the dialkyl ether composition can be recovered by phase separation, or extraction with a suitable solvent, such as trimethylpentane or octane, as is well known in the art. Unreacted 1-butanol can be recovered following separation of the dialkyl ether composition and used in subsequent reactions.

An embodiment of the present invention provides a process as described above, but where the reactant comprises both ethanol and methanol.

Ethanol can be obtained as described above. Methanol can be obtained from traditional chemical sources or can be biomethanol, which can be made, for example from synthesis gas derived from biomass.

The reactant comprising both ethanol and methanol (which may be diluted with an inert gas such as nitrogen, carbon dioxide, or mixtures thereof) is contacted with at least one base catalyst, where the base catalyst is defined as described above, in the vapor or liquid phase at a temperature of about 150° C. to about 500° C. and at a pressure from about 0.1 MPa to about 20.7 MPa to produce a first reaction product comprising at least one $C_3$-$C_{10}$ straight-chain or branched alkyl alcohol. Typically, the first reaction product will also comprise unreacted ethanol and/or methanol, as well as water.

The catalytic conversion of the reactant, wherein the reactant comprises ethanol and methanol, to the first reaction product and water can be run in either batch or continuous mode as described above. Suitable reactors include fixed-bed, adiabatic, fluid-bed, transport bed, and moving bed. During the course of the reaction, the catalyst may become fouled, and therefore it may be necessary to regenerate the catalyst. Preferred methods of catalyst regeneration include contacting the catalyst with a gas such as, but not limited to, air, steam, hydrogen, nitrogen or combinations thereof, at an elevated temperature.

The contacting of the first reaction product can optionally be subjected to a suitable refining process, such as distillation, to remove a substantial portion of the water present in the first reaction product, or to remove unreacted ethanol and/or methanol. If the first reaction product is subjected to a refining process, the resulting product is referred to hereinafter as the "refined first reaction product".

One skilled in the art will know that conditions, such as temperature, catalytic metal, support, reactor configuration and reaction time can affect the reaction kinetics, product yield and product selectivity. Consequently standard experimentation can be used to optimize the yield of alcohols in the first reaction product.

The present invention further contemplates a process for making a dialkyl ether composition comprising two or more ethers of the formula $R^3$—O—$R^4$. The present invention further contemplates a process for making a dialkyl ether composition starting with a mixture of alkyl alcohols independently between $C_1$ and $C_{10}$, straight-chain or branched; more specifically a mixture of ethanol and methanol. The present invention further contemplates a process for making a dialkyl ether composition from a first reaction product of an alcohol, or a mixture of alkyl alcohols independently of any carbon chain length; specifically, an alcohol or a mixture of alkyl alcohols independently between $C_3$ and $C_{10}$, straight-chain or branched, in size. The invention further contemplates a dialkyl ether composition comprising two or more ethers of the formula $R^3$—O—$R^4$, where each $R^3$ and $R^4$ can independently be any carbon chain length, saturated or unsaturated; branched or straight-chain, of between $C_1$ and $C_{10}$; specifically between $C_4$ and $C_{10}$; more specifically between $C_4$ and $C_6$; more specifically $C_6$; more specifically $C_4$. The present invention further contemplates a process from a first reaction product of an alcohol, or a mixture of alcohols, independently of any carbon length; specifically, an alcohol or a mixture of alkyl alcohols independently between $C_3$ and $C_{10}$, straight-chain or branched, used to produce a dialkyl ether composition where each $R^3$ and $R^4$ can independently be any carbon chain length, saturated or unsaturated; branched or straight-chain, of between $C_1$ and $C_{10}$; specifically between $C_4$ and $C_{10}$; more specifically between $C_4$ and $C_6$; more specifically $C_6$; more specifically $C_4$. The present invention further contemplates a process from a first reaction product of an alcohol, or a mixture of alkyl alcohols, specifically, an alcohol or a mixture of alkyl alcohols independently between $C_4$ and $C_6$, straight-chain or branched, to form a dialkyl ether composition, where each $R^3$ and $R^4$ can independently be any carbon chain, saturated or unsaturated; branched or straight-chain, with a length of between $C_1$ and $C_{10}$; specifically between $C_4$ and $C_{10}$; more specifically between $C_4$ and $C_6$; more specifically $C_6$; more specifically $C_4$.

The first reaction product or refined first reaction product with the acid catalyst can be performed at a temperature of from about 50° C. to about 450° C. In a more specific embodiment, the temperature is from about 100° C. to about 250° C. The reaction can be carried out under an inert atmosphere at a pressure of from about atmospheric pressure about 0.1 MPa to about 20.7 MPa. In a more specific embodiment, the pressure is from about 0.1 MPa to about 3.45 MPa. Suitable inert gases include nitrogen, argon, helium, or mixtures thereof.

One skilled in the art will know that conditions, such as temperature, catalytic metal, support, reactor configuration and reaction time can affect the reaction kinetics, product yield and product selectivity. Depending on the reaction conditions, such as the particular catalyst used, products other than dialkyl ethers may be produced when the first reaction product or refined first reaction product is contacted with an acid catalyst. Additional products produced comprise butenes and isooctenes. Standard experimentation can be used to optimize the yield of dialkyl ethers from the reaction.

Following the reaction, if necessary, the catalyst can be separated from the second reaction product by any suitable technique known to those skilled in the art, such as decantation, filtration, extraction or membrane separation.

The dialkyl ether composition can be recovered from the reaction product by distillation. Alternatively, the dialkyl ether composition can be recovered by phase separation, or extraction with a suitable solvent, such as trimethylpentane or octane, as is well known in the art. Unreacted alkyl alcohol can be recovered following separation of the dialkyl ether composition and used in subsequent reactions.

EXAMPLES

The following Examples used the following acidic catalysts: Amberlyst® 70 (commercially available from Rohm and Haas, Philadelphia, Pa.), 98% $H_2SO_4$ (pure) (commercially available from Alfa Aesar (Ward Hill, Mass.); CBV-3020E Zeolite (commercially available from PQ Corporation (Berwyn, Pa.); 13% Nafion®/$SiO_2$ (commercially available from Engelhard); and H-Mordenite (commercially available from Zeolyst Intl. Valley Forge, Pa.). 1-Butanol, 1-hexanol, and 1-octanol were materials used as well, and each is commercially available from Alfa Aesar Ward Hill, Mass.

General Procedure for the Conversion of 1-Butanol to Dibutyl Ethers

A mixture of 1-butanol and an acid catalyst was contained in a 2 mL vial equipped with a magnetic stir bar. The vial was sealed with a serum cap and perforated with a needle to facilitate gas exchange. The vial was placed in a block heater enclosed in a pressure vessel. The vessel was purged with nitrogen and the pressure was set at 4.8 MPa. The block was brought to the indicated temperature (See Table 1) and controlled at that temperature for the time indicated. After cooling and venting, the contents of the vial were analyzed by GC/MS using a capillary column (either (a) CP-Wax 58 [Varian; Palo Alto, Calif.], 25 m×0.25 mm, 45 C/6 min, 10° C./min up to 200° C., 200° C./10 min, or (b) DB-1701 [J&W (available through Agilent; Palo Alto, Calif.)]), 30 m×0.2 5 mm, 50° C./10 min, 10° C./min up to 250° C., 250° C./2 min).

The examples below were performed according to the above procedure under the conditions indicated for each Example. The Examples used 1-butanol, 1-hexanol and 1-octanol as materials characteristic of the alcohols produced in the condensation reaction. Olefins selectivity is defined as the portion of feed alcohols which yields butenes, hexenes and octenes as byproducts. "Ethers % Selectivity" is the sum of all $C_4$, $C_6$ and $C_8$ carbon chain alcohol based ethers observed in the GC/MS.

Examples 1-4

Reaction of 50:50 by weight 1-butanol (1-BuOH) and 1-hexanol (HeOH) with an Acid Catalyst to Produce Dialkyl Ethers The reactions were carried out for 2 hours at 4.8 MPa of $N_2$ at the indicated temperature. Acidic catalysts used in each case was 50 mg per 1 mL solution in a neat reaction.

TABLE 1

| Example Number | Catalyst (50 mg) | Temp (C.) | Alkanol % Conversion | Olefins % Selectivity | Ethers % Selectivity |
|---|---|---|---|---|---|
| 1 | $H_2SO_4$ (pure) | 200 | 89.0% | 11.9% | 85.6% |
| 2 | 13% Nafion ®/$SiO_2$ | 200 | 33.0% | 1.7% | 96.9% |
| 3 | CBV-3020E | 200 | 79.4% | 14.7% | 80.3% |
| 4 | H-Mordenite | 200 | 46.4% | 15.3% | 74.3% |

Examples 5-6

A mixture of 50% (by weight) 1-BuOH, 30% MeOH and 20% 1-octanol ($C_8OH$) was reacted under the same conditions as above Examples 1-4 with the following results indicated in Table 2 below. The amount of catalyst used in each case was 50 mg per 1 mL solution in a neat reaction.

TABLE 2

| Example Number | Catalyst (50 mg) | Temp (C.) | Alkanol % Conversion | Olefins % Selectivity | Ethers % Selectivity |
|---|---|---|---|---|---|
| 5 | $H_2SO_4$ (pure) | 200 | 97.3 | 9.9 | 84.7 |
| 6 | Amberlyst ® 70 | 200 | 87.2 | 7.1 | 85.8 |

Although particular embodiments of the present invention have been described in the foregoing description, it will be understood by those skilled in the art that the invention is capable of numerous modifications, substitutions, and rearrangements without departing from the spirit or essential attributes of the invention. Reference should be made to the appended claims, rather than to the foregoing specification, as indicating the scope of the invention.

What is claimed is:

1. A process for making a dialkyl ether composition comprising two or more ethers of the formula $R^1$—O—$R^2$, wherein each $R^1$ and $R^2$ is independently $C_2$ - $C_{10}$ straight-chain or branched alkyl groups, comprising:
    a) contacting a reactant comprising ethanol with a base catalyst to make a first reaction product comprising 1-butanol and water, and optionally comprising unreacted ethanol;
    b) optionally removing a substantial portion of the water from said first reaction product;
    c) optionally removing a substantial portion of the unreacted ethanol from said first reaction product;
    d) contacting the product of either step (a), step (b), step (c), or steps (b) and (c), optionally in the presence of a solvent, with at least one acid catalyst at a temperature of about 100° C. to about 250° C. and a pressure 4.8 MPa to produce a second reaction product comprising two or more ethers of the formula $R^1$—O—$R^2$; and
    e) recovering said dialkyl ether composition from said second reaction product, wherein the selectivity to the ethers is at least about 74%.

2. The process of claim 1, wherein each $R^1$ and $R^2$ is independently $C_4$ - $C_{10}$ straight-chain or branched alkyl.

3. The process of claim 1, wherein the acidic catalyst is a homogenous catalyst.

4. The process of claim 1, wherein the acidic catalyst is a heterogeneous catalyst.

5. A process for making a dialkyl ether composition comprising two or more ethers of the formula $R^3$—O—$R^4$, wherein each $R^3$ and $R^4$ is independently $C_1$ - $C_{10}$ straight-chain or branched alkyl groups, comprising:
    a) contacting a reactant comprising ethanol and methanol with a base catalyst to make a first reaction product comprising at least one $C_3$ - $C_{10}$ straight-chain or branched alkyl alcohol and water, and optionally comprising unreacted reactant;
    b) optionally removing a substantial portion of the water from said first reaction product;
    c) optionally removing a substantial portion of the unreacted reactant from said first reaction product;
    d) contacting the product of either step (a), step (b), step (c), or steps (b) and (c), optionally in the presence of a solvent, with at least one acid catalyst at a temperature of about 100° C. to about 250° C. and a pressure 4.8 MPa to produce a second reaction product comprising two or more ethers of the formula $R^3$—O—$R^4$; and
    e) recovering said dialkyl ether composition from said second reaction product, wherein the selectivity to the ethers is at least about 74%.

6. The process of claim 5, wherein each $R^1$ and $R^2$ is independently $C_4$ - $C_6$ straight-chain or branched alkyl.

7. The process of claim 5, wherein each $R^1$ and $R^2$ is independently $C_6$ chain or branched alkyl.

8. The process of claim 5, wherein each $R^1$ and $R^2$ is independently $C_4$ straight-chain or branched alkyl.

9. The process of claim 5, wherein the acidic catalyst is a homogenous catalyst.

10. The process of claim 5, wherein the acidic catalyst is a heterogeneous catalyst.

* * * * *